United States Patent [19]

Massé et al.

[11] 4,379,407
[45] Apr. 12, 1983

[54] SYSTEM FOR CONDUCTING RESONANCE MEASUREMENTS OF ROCK MATERIALS UNDER CONFINING PRESSURE

[75] Inventors: Lucien Massé; William L. Medlin, both of Dallas; James H. Sexton, Duncanville, all of Tex.

[73] Assignee: Mobil Oil Corporation, New York, N.Y.

[21] Appl. No.: 259,775

[22] Filed: May 1, 1981

[51] Int. Cl.³ .............................................. G01N 29/00
[52] U.S. Cl. ...................................................... 73/579
[58] Field of Search ................. 73/579, 571, 597, 574, 73/576, 573, 808, 811, 789, 794

[56] References Cited

U.S. PATENT DOCUMENTS

| | | | |
|---|---|---|---|
| 1,414,077 | 4/1922 | Fessenden | 73/579 |
| 3,320,796 | 5/1967 | Darby | 73/576 |
| 3,489,161 | 1/1970 | Rexford | 73/579 |
| 4,058,007 | 11/1977 | Exner | 73/DIG. 1 |

OTHER PUBLICATIONS

"A Review of the Progress in the Measurement of Dynamic Elastis Properties", Hillier, Imperial Chem. Industries Ltd., pp. 183-199.
"The Attenuation Constant of Earth Materials", Born, pp. 132-147.
"Effects of Pressure & Fluid Saturation on the Attenuation of Elastic Waves in Sands", Gardner et al., Petroleum Transactions, pp. 189-199, Feb. 1964, J. of Petroleum Technology.

Primary Examiner—Anthony V. Ciarlante
Attorney, Agent, or Firm—Charles A. Huggett; Michael G. Gilman; George W. Hager

[57] ABSTRACT

A confining pressure system includes a pressure cell containing a mechanical oscillator and a gas supply for carrying out resonance measurements of rock material under confining pressure at seismic frequencies. An appropriate gas is used to avoid significant damping of oscillations under confining pressures of various ranges.

2 Claims, 4 Drawing Figures

SYSTEM FOR CONDUCTING RESONANCE MEASUREMENTS OF ROCK MATERIALS UNDER CONFINING PRESSURE

BACKGROUND OF THE INVENTION

Many seismic investigation techniques have been developed. For the most part these investigations have been guided by three main sources of data: field seismic records, well logs, and laboratory measurements of ultrasonic pulse velocities in core samples of rock materials. With respect to ultrasonic pulse velocity measurements the travel time of an ultrasonic wavelet is measured between ends of a cylindrical or prismatic bar of rock material. Experimental techniques require a signal wavelet which has died out at the excitation end before it is detected at the receiving end. For samples of practical length this requires a signal frequency of the order of hundreds of kHz. Seismic data are limited to frequencies below a few hundred hertz. Consequently the ultrasonic pulse velocity technique has not permitted measurements at frequencies approaching the seismic range.

SUMMARY OF THE INVENTION

In accordance with the present invention, there is disclosed a confining pressure system for making resonance measurements of rock materials under a confining pressure.

The confining pressure system includes a pressure cell containing a mechanical oscillator and a gas supply for adjusting the confining pressure using gases which do not introduce significant viscous damping of the oscillations. The pore pressure within the rock sample is controlled independently of the confining pressure by means of a separate gas supply applied directly to the rock sample itself.

DESCRIPTION OF THE PREFERRED EMBODIMENT

The present invention relates to a system for measuring resonance characteristics of rock material at seismic frequencies under confining pressure from which wave velocities and attenuation coefficients can be determined.

First, the mechanical oscillator system will be described in conjunction with FIGS. 1-2, then the confining pressure system will be described in conjunction with FIGS. 3-4.

MECHANICAL OSCILLATOR SYSTEM

Figure 1:
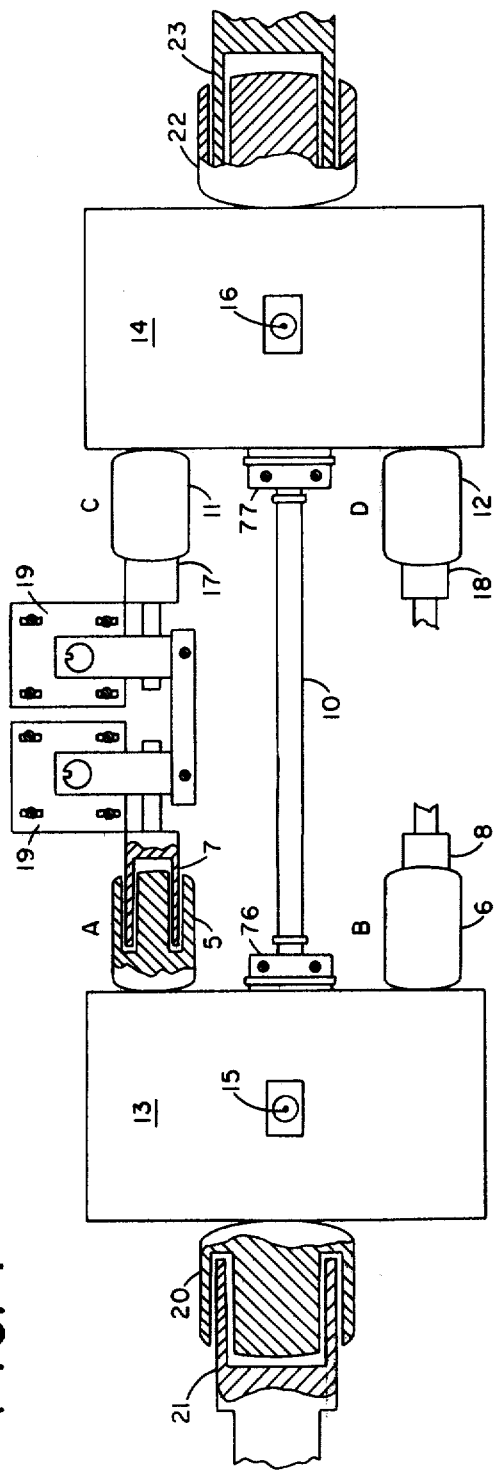
FIG. 1 illustrates a mechanical oscillator system.
Figure 2:
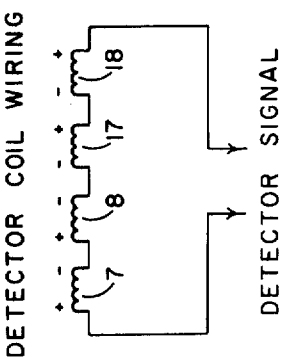
FIG. 2 illustrates a detection system for use in measuring displacements of the masses of the mechanical oscillator of FIG. 1.

Referring now to FIG. 1, the mechanical oscillator utilizes the concept of a mass-spring system with a rock sample acting as the spring. The resonant frequency is determined not only by the dimensions of the rock, which control the spring constant, but by the mass, which can be made very large. By using a large enough mass, resonant frequencies in the seismic range are produced with rock samples from 6 to 10 inches in length. From the resonant frequency the spring constant and Youngs modulus of the rock can be determined. An advantage of this method is that it is not necessary to make measurements far below the resonant frequency or to use samples of impractical dimensions to operate in the seismic frequency range. The spring-mass system can also be constructed so as to keep parasitic damping negligibly low. Since the dynamic properties of many rock materials are amplitude sensitive, it is important that the amplitude of oscillation be kept at or near seismic levels which is also possible by this method.

The rock sample 10 is clamped in a horizontal position between the two masses 13 and 14 which are suspended from a fixed support (not shown) by means of the wires 15 and 16 respectively. The support is seismically isolated from the earth. Mass 13 is attached to a permanent magnet 20 while mass 14 is attached to a permanent magnet 22. Driving coils 21 and 23 are positioned in the air gaps of the magnets 20 and 22, respectively to provide a conventional means for applying driving forces to the masses 13 and 14. A sinusoidal signal of frequency f is applied to each coil with the appropriate polarity to drive the masses in opposition.

The system has two natural modes of vibration, a high frequency one in which the two masses, 13 and 14, move in opposite directions and a lower frequency one in which they move in the same direction. Longitudinal oscillations are produced in the rock sample 10 when the masses move in opposition. This condition is favored when the system is symmetrical, that is, when the masses 13 and 14 are equal, the lengths of wires 15 and 16 are equal, the driving currents to the coils 21 and 22 are equal, and the magnetic field strengths in the air gaps of the magnets are equal. Under such conditions, the low frequency mode is largely eliminated and there is a single prominent resonance.

Resonance measurements require a method for measuring the displacements $X_1$ and $X_2$ of the masses 13 and 14, respectively, or their difference. One method for measuring the relative displacement $|X_1 - X_2|$ is illustrated in FIG. 1. A pair of identical permanent magnets 5 and 6 are attached to the mass 13 and a pair of identical permanent magnets 11 and 12 are attached to the mass 14 with their axes lying in a plane perpendicular to the plane of the wire supports, 15 and 16. Identical coils 7, 8, 17 and 18 are positioned in the air gaps of each of the magnets 5, 6, 11 and 12 respectively. These coils are rigidly mounted on the oscillator frame through alignment brackets, 19. Motion of the masses produces an emf in the detector coils. By connecting the coils in series with appropriate polarity as shown in FIG. 2, the signals due to motion of the masses in opposition add and give an emf proportional to $|X_1 - X_2|$.

CONFINING PRESSURE SYSTEM

Figure 3:
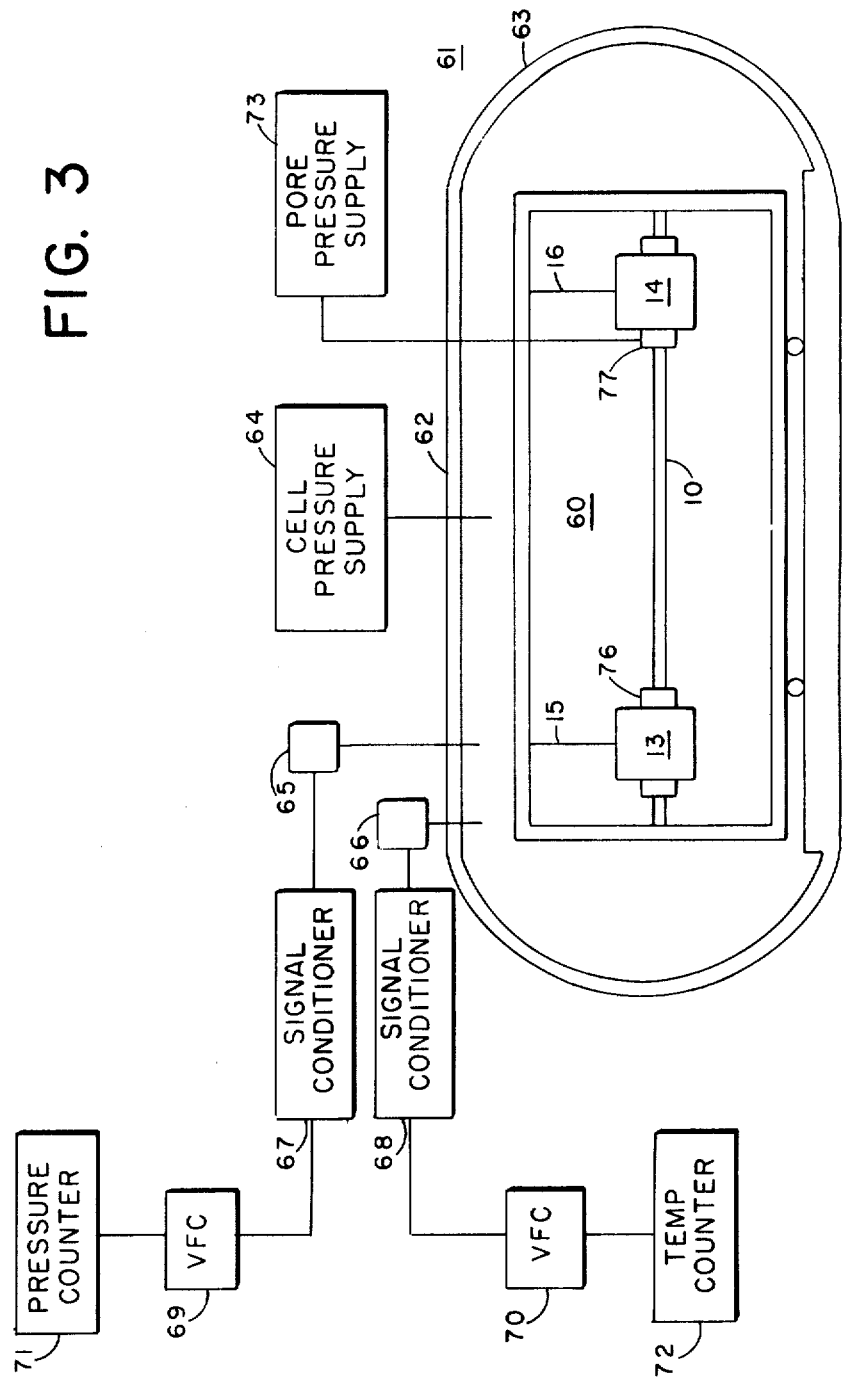
FIG. 3 shows the confining pressure cell with monitoring equipment in which the mechanical oscillator of FIG. 1 will operate.
Figure 4:
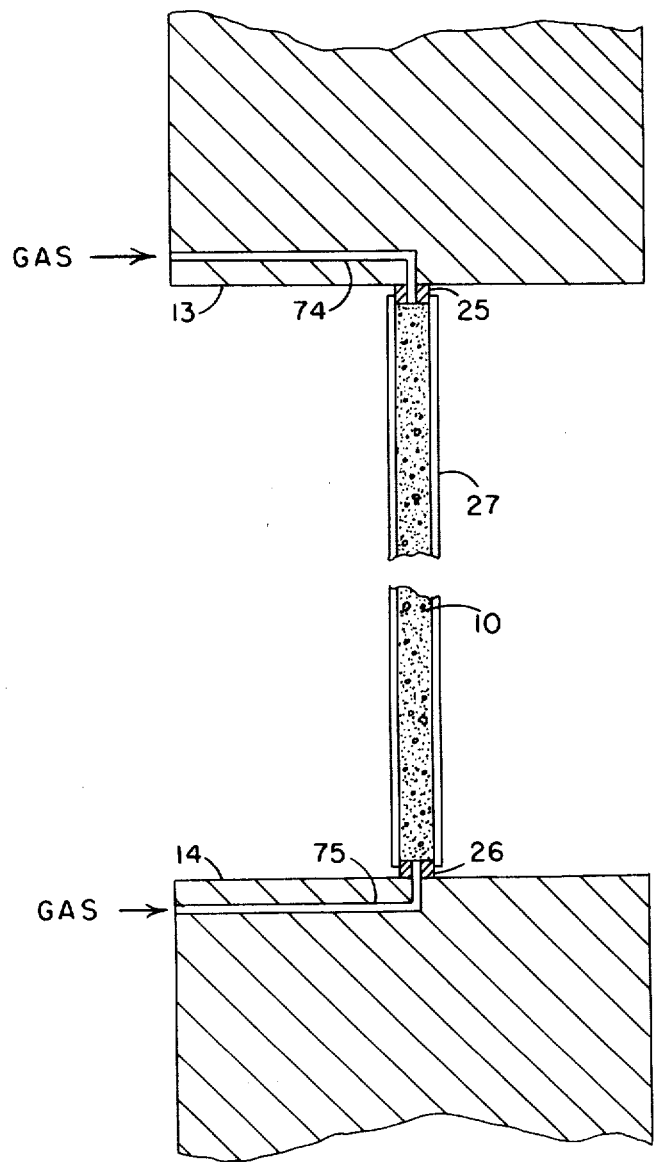
FIG. 4 shows the gas flow path to the rock sample for controlling pore pressure within the rock sample.

Referring now to FIG. 3, the complete oscillator system 60 is enclosed in a large steel pressure cell 6 for conducting resonance measurements under a confining pressure. One such cell, manufactured by Melco Steel, Inc., Paramount, Calif., comprises a cylindrical vessel 62 with spherical ends 63. Inside diameter is about 18 inches and cylinder length is about 36 inches. One end piece is a hinged door, fitted with a ring seal, through which the oscillator system 60 may be inserted or rolled on wheels or tracks into the cell.

A suitable gas supply 64 introduces a desired confining pressure into the cell 61. Nitrogen gas can be used to provide confining pressures up to 2000 p.s.i. without introducing significant viscous damping of the mass vibrations in the oscillator system. Above 2000 p.s.i. helium gas can be used to provide the confining pressure without introducing significant damping in the oscillator system. A pressure transducer 65, preferably a type DHF pressure transducer supplied by Baldwin-Lima-Hamilton Corporation, Waltham, Mass., measures the confining pressure inside the cell, while a standard thermistor 66 measures cell temperature. Electrical feed throughs are provided through the cell wall 62 by means of standard Conax fittings.

Signal conditioners 67 and 68 convert the pressure and temperature measurements respectively into dc voltage signals. These dc voltage signals are applied to the voltage-to-frequency converters 69 and 70 which produce pulses whose frequency is proportional to pressure and temperature, respectively. Counters 71 and 72 count such pulses to provide the desired pressure and temperature readings respectively.

Another suitable gas supply 73 may be used to control pore pressure within the rock sample 10 independently of the confining cell pressure. As shown in FIG. 4, gas is introduced into rock sample 10, through passage ways or capillary tubings 74 and 75 in masses 13 and 14 respectively and through steel end caps 25 and 26. The rock sample 10 is attached to the end caps 25 and 26 by means of a hard epoxy bond. Each end cap contains a 6-32 threaded port in communication with the rock sample. These end caps are used to clamp the rock sample to the masses 13 and 14 by means of the steel clamping fixtures 76 and 77 as shown in FIG. 1. The rock sample 10 is sealed with a heat shrinkable jacket 27. Epoxy beads are used to seal the edges of the jacket overlapping the end caps.

While the harmonic oscillator and confining pressure system of the present invention has been shown and described, additional modifications are within the spirit and scope of the invention. The appended claims are intended to cover all such modifications.

What is claimed is:

1. In a system for measuring resonance characteristics of rock material under an oscillatory driving force, the improvement comprising:
    (a) means for enclosing said rock material under confining pressure,
    (b) means for adjusting the confining pressure without introducing significant viscous damping in the oscillations, and
    (c) means for controlling pore pressure within said rock material independently of said confining pressure.

2. The system of claim 1 wherein said pore pressure controlling means includes:
    (a) a gas supply, and
    (b) a passage way connecting said gas supply to at least one end of said rock material.

* * * * *